(12) United States Patent
Kendurkar et al.

(10) Patent No.: US 10,131,698 B2
(45) Date of Patent: Nov. 20, 2018

(54) SYNTHETIC ANTIMICROBIAL PEPTIDES (71) Applicant: COUNCIL OF SCIENTIFIC & INDUSTRIAL RESEARCH, New Delhi (IN)

(72) Inventors: Shuchishweta Vinay Kendurkar, Maharashtra (IN); Durba Sengupta, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/503,899

(22) PCT Filed: Aug. 13, 2015

(86) PCT No.: PCT/IN2015/050093
§ 371 (c)(1),
(2) Date: Feb. 14, 2017

(87) PCT Pub. No.: WO2016/024296
PCT Pub. Date: Feb. 18, 2016

(65) Prior Publication Data
US 2018/0141987 A1    May 24, 2018

(30) Foreign Application Priority Data
Aug. 14, 2014 (IN) .......................... 2320/DEL/2014

(51) Int. Cl.
| | | |
|---|---|---|
| *A61K 38/08* | (2006.01) | |
| *A61K 38/10* | (2006.01) | |
| *A61K 38/04* | (2006.01) | |
| *C07K 16/12* | (2006.01) | |
| *C07K 16/14* | (2006.01) | |
| *C07K 7/00* | (2006.01) | |
| *C07K 7/06* | (2006.01) | |
| *C07K 7/08* | (2006.01) | |
| *C07K 14/47* | (2006.01) | |

(52) U.S. Cl.
CPC .......... *C07K 14/4723* (2013.01); *A61K 38/08* (2013.01); *A61K 38/10* (2013.01); *C07K 7/06* (2013.01); *C07K 7/08* (2013.01); *Y02A 50/473* (2018.01); *Y02A 50/481* (2018.01)

(58) Field of Classification Search
CPC .... C07K 14/4723; C07K 16/12; C07K 16/14; C07K 7/00; C07K 7/06; C07K 7/08; A61K 38/08; A61K 38/10; A61K 38/04
USPC ... 514/1.1, 2.3, 2.4, 2.7, 3.3, 3.4, 21.4, 21.6; 530/300, 326, 328
See application file for complete search history.

(56) References Cited

U.S. PATENT DOCUMENTS

| | | | | |
|---|---|---|---|---|
| 5,686,563 | A * | 11/1997 | Kari .......................... | C07K 7/08 530/326 |
| 7,091,185 | B2 * | 8/2006 | Strom .................. | C07K 14/001 514/2.4 |
| 7,713,927 | B2 * | 5/2010 | He .......................... | A61K 8/64 514/1.1 |

FOREIGN PATENT DOCUMENTS

| | | |
|---|---|---|
| WO | WO 2012/057713 A1 | 5/2012 |
| WO | WO 2013/033838 A1 | 3/2013 |

OTHER PUBLICATIONS

International Search Report (ISR) for PCT/IN2015/050093; I.A. fd: Aug. 13, 2015, dated Feb. 5, 2016, European Patent Office, Rijswijk, Netherlands.
International Preliminary Report on Patentability (IPRP) including the Written Opinion of the International Searching Authority (PCT Rule 44bis) for PCT/IN2015/050093; I.A. fd: Aug. 13, 2015, dated Feb. 14, 2017, by the International Bureau of WIPO, Geneva, Switzerland.

\* cited by examiner

*Primary Examiner* — Julie Ha
(74) *Attorney, Agent, or Firm* — Sterne, Kessler, Goldstein & Fox P.L.L.C.

(57) ABSTRACT

Anti-microbial compositions comprising synthetic peptides for therapeutic use are described. These compositions have found applications in treating human and plant infections.

16 Claims, 5 Drawing Sheets
Specification includes a Sequence Listing.

(iii)

SYNTHETIC ANTIMICROBIAL PEPTIDES

REFERENCE TO SEQUENCE LISTING SUBMITTED ELECTRONICALLY

The content of the electronically submitted substitute sequence listing, file name 3734_0080001_SeqListing.txt, size 1,097 bytes; and date of creation Jun. 5, 2017, filed herewith, is incorporated herein by reference in its entirety.

TECHNICAL FIELD OF THE INVENTION

The present invention relates to an anti-microbial composition comprising synthetic peptides for therapeutic use as anti-bacterial and anti-fungal agents in plants and animals.

BACKGROUND AND PRIOR ART OF THE INVENTION

Development of antimicrobial peptides (AMPs) as novel therapeutics has garnered interest in view of the increasing threat of multiple drug resistant micro-organisms coupled with the lack of new synthetic antimicrobial chemicals. Antimicrobial peptides play a key role in the functioning of a host's innate defense system against infections in most mammalians (Boman H G et al *Annu. Rev. Immunol.* 13:61-92). The potential therapeutic applications of AMPs are characterized by their broad-spectrum antibacterial activity. It would be extremely difficult for multi-drug/fungicide resistant micro-organisms to evolve resistance against AMPs that disrupt the microbial membrane, since it would necessitate fundamental alterations in the lipid composition of the bacterial membranes.

Diseases caused by fungi, bacteria and viruses are of major concern to human health and to agricultural produce due to the heavy crop losses incurred by fungal infestations. Chemical drugs and solutions used to evade diseases cause extensive deterioration in environment quality and a rise in resistant organisms. Therefore, there is an increase in the need for safe and effective antimicrobial agents with expanding number of immunocompromised patients at risk for invasive fungal infections. AMPs (antimicrobial peptides) have been considered as novel therapeutics in combating the increasing incidence of antibiotic resistance in pathogenic microbes and several examples are undergoing clinical trials.

Nature provides the answer in the form of antimicrobial peptides that are not only lethal to a broad spectrum of pathogens but also have a unique low tendency for resistance development. A variety of antimicrobial peptides and proteins have been isolated from virtually all the kingdoms and phyla including plants, microbes, insects, animals and humans. Rational design of novel non-natural AMPs can be targeted to enhance stability, potency and specificity towards selected microbes. Short sequence length of these AMPs facilitates design of synthetic genes, and incorporation into plants through genetic engineering. These are unique candidate target peptides (probiotic), which are often half the size of natural counterparts (10-20 Amino Acids) and are active at low concentrations without toxicity to host tissues. In many cases, synthetic analogs of natural antimicrobial peptides offer even more target specificity, increased efficacy at lower concentration, and reduced degradation by plant proteases than their natural counterparts.

In a research study 'Design and engineering strategies for synthetic antimicrobial peptides' (*Prokaryotic Antimicrobial Peptides* 2011, pp 81-98) A. Tossi reveals an important feature in the mode of action of AMPs is their dynamic interaction with biological membranes, which involves properties of these peptides such as, surface hydrophobicity and polarity, charge, structure, and induced conformational variations which are often intimately interconnected; hence engineering peptides to independently adjust any one property in particular is not an easy task. However, solid-phase peptide synthesis allows the use of a large repertoire of non-proteinogenic amino acids that can be used in the rational design of peptides to finely tune structural and physicochemical properties.

In Indian Patent Application No. 1010/DEL/2006, the preparation and antimicrobial activities of hexapeptides, which offer an improved means for the treatment and prevention of fungal and bacterial infections is disclosed. The development of these peptides provides for the treatment and control of opportunistic fungal infections. However, no references to the stability of the hexapeptides are provided, which is integral to the systemic administration and functioning of the peptides. Furthermore, synthetic peptides disclosed in the Indian application include the use of non-natural amino acids such as ornithine which increases the cost of synthetic peptide production, and renders genetic engineering procedures impractical.

Though natural AMPs have many antimicrobial attributes, several studies have exposed their potential limitations as therapeutic agents. A significant number of natural AMPs are large however, exhibit moderate antimicrobial activity. Moreover, their production cost is high. In addition, many natural AMPs lose their antimicrobial activity at higher salt concentrations. These characteristics have substantially weakened their pharmaceutical development as new therapeutic agents. Thus, successful development of novel AMPs as future therapeutics requires identification of short AMPs demonstrating strong antimicrobial activity, high stability and minimal toxicity to host tissue.

Synthetic antimicrobial peptides are being viewed as promising alternatives as novel therapeutics in combating increasing incidence of antibiotic resistance in pathogenic microbes in humans. In addition, AMPs have been shown to be active against plant pathogens. Several AMPs are active against both human and plant pathogens. AMPs that are active against a broad range of pathogens are more desirable and need to be tested against different pathogens to confirm their activity.

In view of a pending need in the art to develop antimicrobial peptides having broad spectrum activity along with favorable characteristics for administration in a subject, the present inventors have devised an anti-microbial composition comprising novel synthetic peptides having activity against bacterial and fungal pathogens.

OBJECTIVE OF THE INVENTION

The defining objective of the present invention is to provide novel synthetic therapeutics in combating the increasing incidence of antibiotic resistance in pathogenic microbes.

Another objective of the present invention is to provide an anti-microbial composition comprising novel synthetic peptides.

Yet another objective of the present invention is to provide an anti-microbial composition comprising of synthetic peptides having low molecular weight to overcome permeability issues, minimal cytotoxicity to host tissues, and high stability.

SUMMARY OF THE INVENTION

The present invention provides an anti-microbial composition comprising of synthetic peptides for therapeutic applications in human infections and as well as against fungal parasites infecting plants.

In one aspect, the present invention provides an anti-microbial composition comprising one or more synthetic peptides selected from the group consisting of SEQ. ID. NO: 1, SEQ. ID. NO: 2 and SEQ. ID. NO: 3, (as provided in Table 1) for therapeutic uses ranging from treatment and prevention of bacterial and fungal infections in plants and animals.

In another aspect, the present invention provides an anti-microbial composition comprising cationic synthetic peptides having alpha helical and coil characteristics.

In one more aspect, the present invention provides an anti-microbial composition comprising of synthetic peptides exhibiting inhibitory activity characterized by antifungal mechanisms such as membrane damage and reactive oxygen species generation.

In yet another aspect, the present invention provides that the instant anti-microbial composition inhibit the activity of pathogenic micro-organisms selected from the group consisting of bacterial pathogens such as *Staphylococcus aureus, Pseudomonas aeruginosa, Escherichia coli* and *Salmonella enterica* and fungal human pathogens, *Candida albicans, Cryptococcus neoformans, Aspergillus niger* and fungal plant pathogens, *Fusarium oxysoprum, Neurospora crassa* and *Ustilago maydis*.

| Micro-organism | NCIM | ATCC |
|---|---|---|
| Candida albicans | 3557 | 24433 |
| Cryptococcus neoformans | 3542 | 34664 |
| Aspergillus niger | 628 | 10578 |
| Fusarium oxysoprum | 1043 | |
| Neurospora crassa | 1001 | 10333 |
| Ustilago maydis | 983 | |
| Staphylococcus aureus | 2079 | |
| Pseudomonas aeruginosa | 2074 | |
| Escherichia coli | 2065 | 8739 |
| Salmonella enterica | 5256 | 12011 |

Further, the said synthetic peptides constituting the present anti-microbial composition are synthesized by solid phase peptide synthesis.

DETAILED DESCRIPTION OF THE FIGURES

DETAILED DESCRIPTION OF THE INVENTION

The invention will now be described in detail in connection with certain preferred and optional embodiments, so that various aspects thereof may be more fully understood and appreciated.

In a preferred embodiment, the present invention provides an anti-microbial composition comprising one or more synthetic peptides selected from the group consisting of SEQ. ID. NO: 1, SEQ. ID. NO: 2 and SEQ. ID. NO: 3.

Accordingly, the antimicrobial peptides disclosed in the present invention are short peptides having chain length of 9 amino acids and 17 amino acids. Presently, short AMPs that minimize damage to host cells or tissues appear to be the most promising candidates for large-scale production (Strom M B et al; 2003 *J. Med. Chem.* 46:1567-1570).

In one embodiment, the present invention provides pharmaceutically acceptable excipients selected from a solvent, a viscosity imparting agent, a buffering agent, and a humectant.

Accordingly, the solvent is selected from the group consisting of water, ethanol, isopropanol and propanol, the viscosity imparting agent is selected from the group consisting of hydroxyethyl cellulose, or hydroxypropyl methylcellulose, and buffering agent is selected from the group consisting of fumarates, carbonates, phosphates, and gluconates having pH in the range of 4 to 7.

Additionally a preservative selected from benzoic acid, methyl paraben, ethyl paraben and propyl paraben is also added to the present composition.

The present antimicrobial composition may be administered to a subject as tablets, capsule, or gels, pellets, granules, oral and injectable powders, ointments, syrups, solutions, liquid ampoules, dispersions, aerosol sprays, semi-solids, softgels, aerosols, and suspensions including nano and micro suspensions.

Further, the present synthetic peptides are optimized based on physicochemical properties selected from the group consisting of molecular weight, net charge, isoelectric point, aliphatic index, instability index, probability of forming an antimicrobial peptide, mean hydrophobic moment, mean hydrophobicity, % hydrophobic residues and helix propensity.

In an embodiment, the present invention provides the net charge on the present synthetic peptides in the range of 3 to 10.

Ideally peptides varying from 10 to 150 amino acids have a net charge between −3 and +20 and a hydrophobic content below 60%. (Table 2) The net charge and positively charged residues on polar face significantly affects α-helical AMPs' antimicrobial activity and hemolytic activity, thereby enhancing the anti-microbial properties of the present composition.

In another embodiment, the present invention provides synthetic peptides having molecular weight in the range of 1000 to 2100 Da.

Anti-microbial synthetic peptides with a smaller molecular weight are more conducive and convenient for administration procedures and prevent interference and damage to body tissue or other organs.

In yet another embodiment, the present invention provides synthetic peptides having a high aliphatic index and a low instability index which contributes to the stability of the present peptides and therefore the present anti-microbial composition. (Table 3) A high aliphatic index and a low instability index value are preferable for a peptide.

The present anti-microbial peptides have a high aliphatic index and a low instability index value, thereby indicating the stability of the present synthetic peptides in differing conditions including body temperature and body fluid pH.

Table 4 indicates the probability of the peptides to have antimicrobial propensity, wherein this range is measured to be between 0 to 1, which is ideal for anti-microbial peptides. Table 5 indicates the hydrophobic moment of the instant peptides.

In view of the physico-chemical properties of the present peptides, the present anti-microbial composition comprising the said peptides is administered to individuals at a target site to prevent or for the treatment of a disease.

The present peptides have been designed considering the essential structural features required for synthesizing a functional antimicrobial peptide. Lack of sequence or structural homology in native sequences makes it challenging to design potent synthetic antimicrobial peptides with the desired activities or to predict the activity of peptides in vivo.

A comparison of AMP sequences by Brown K. L et al reveals that two types of side chains are essential for antimicrobial activity. The cationic side chains arginine (R), lysine (K), and histidine (H) are thought to mediate peptide interactions with negatively charged membranes and/or cell walls of bacteria, including lipopolysaccharide (2006 *Curr. Opin. Immunol.* 18:24-30). Considering these findings synthetic peptides have been synthesized employing the Solid Phase Peptide synthesis (SPPS) method. The present synthetic anti-microbial peptides selected from SEQ. ID. NO: 1, SEQ. ID. NO: 2 and SEQ. ID. NO: 3 are referred to as ModPep, Martian and Modified Martian respectively. These linear amino acid sequences are disclosed in Table 1 below of the instant invention.

In another preferred embodiment, the present invention provides an anti-microbial composition comprising synthetic peptides selected from one or more amino acid sequences i.e. SEQ. ID. NO: 1, SEQ. ID. NO:2 and SEQ. ID. NO: 3, wherein each of the said peptides are cationic having helical and coil structures.

In accordance with the above embodiment, circular dichroism (CD) spectroscopy performed to determine the structural features of the synthetic peptides constituting the present composition indicated that the said peptides consist of α-helix and coil structures.

Alpha-helix, beta-sheet, and random coil structures each give rise to a characteristic shape and magnitude of CD spectrum. The alpha helix in a protein has negative bands at 222 nm and 208 nm and a positive one at 190 nm; and a beta sheet shows a negative band at 218 nm and a positive one at 196 nm. Random coil has a positive band at 212 nm and a negative one around 195 nm. The server Dicoro web K2D3 was used to perform the online analysis of circular dichroism spectroscopy.

Figure 4:
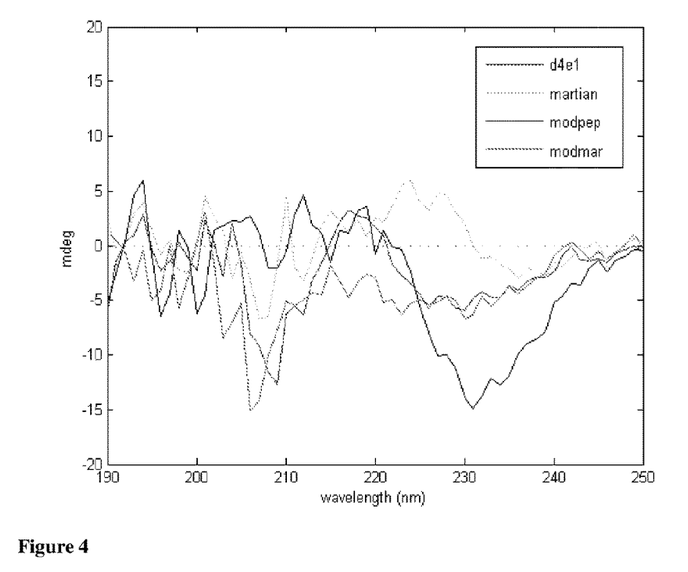
FIG. 4 depicts the circular dichroism data.
Figure 5:
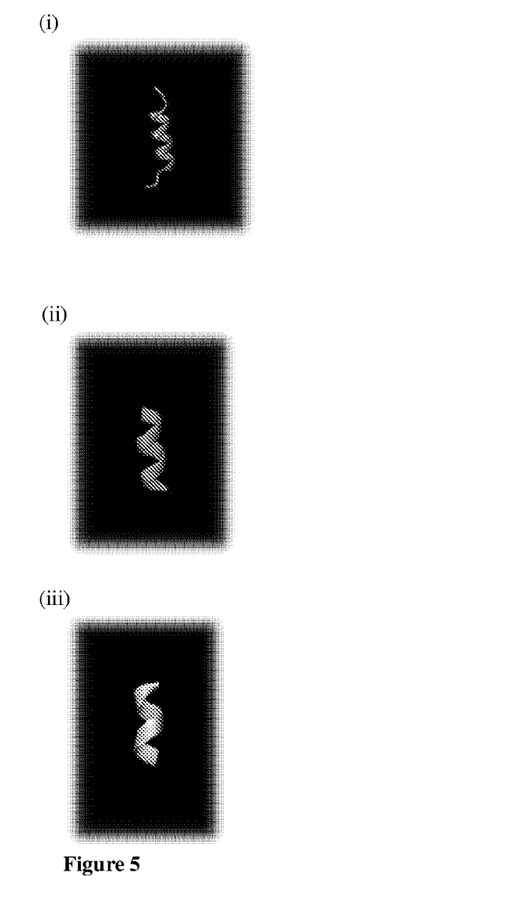
FIG. 5 depicts the following in-silico synthesized protein structures (i) ModPep peptide, (ii) Martian peptide and (iii) Modified Martian peptide.

Analysis of the positive and negative bands in FIG. 4, reveal that the instant peptides predominantly are composed of α-helix and coil characteristics.

In one more preferred embodiment, the invention provides for the synthesis of the said synthetic anti-microbial peptides by Solid phase peptide synthesis (SPPS).

SPPS involves repeated cycles of coupling, washing, de-protection of the alpha amino group of the amino acid and washing.

Accordingly, a single cycle in the process comprises:
a) Adding a cleaving agent (TFA (trifluoroacetic acid) (95%), water (2.5%), and TIS (triisopropylsilane) (2.5%) to the template amino acid sequence to cleave the alpha amino protecting group and washing away the excess cleavage reagent;
b) Coupling of the protected amino acid by DIC (N,N'-diisopropylcarbodiimide) and HOBt (N-hydroxybenzotriazole);
c) Confirming purity studies through reverse phase-HPLC;
d) Mass analysis to determine the mass of the peptide; and
e) Lyophilizing the peptide.

SPPS involves repeated cycles of coupling-wash-deprotection-wash. The free N-terminal amine of a solid-phase attached peptide is coupled to a single N-protected amino acid unit. This unit is then deprotected, revealing a new N-terminal amine to which a further amino acid may be attached. The solid phase peptide synthesis uses the F-moc method. On performing wash cycles after each reaction, excess reagent is removed and the growing peptide of interest remaining covalently attached to the insoluble resin.

In yet another preferred embodiment, the present invention provides that the said peptides having sequences of SEQ. ID. NO: 1, SEQ. ID. NO: 2 and SEQ. ID. NO: 3, bind to the bilayer of a microbial cell wall, subsequently inhibiting cellular activity.

Figure 1:
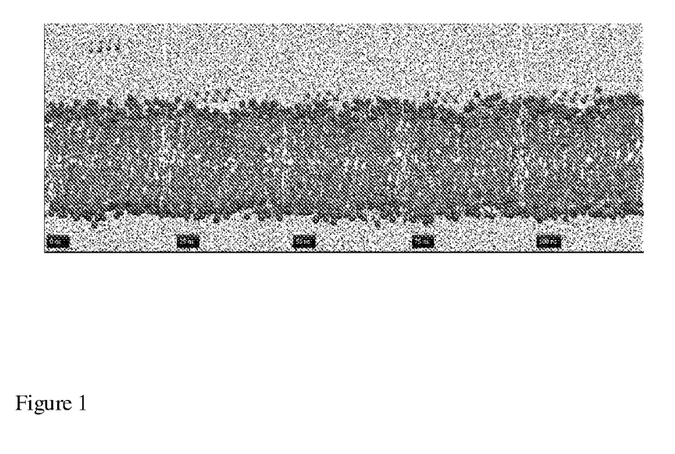
FIG. 1 depicts the binding of ModPep peptide to the head groups of lipid chains.
Figure 2:
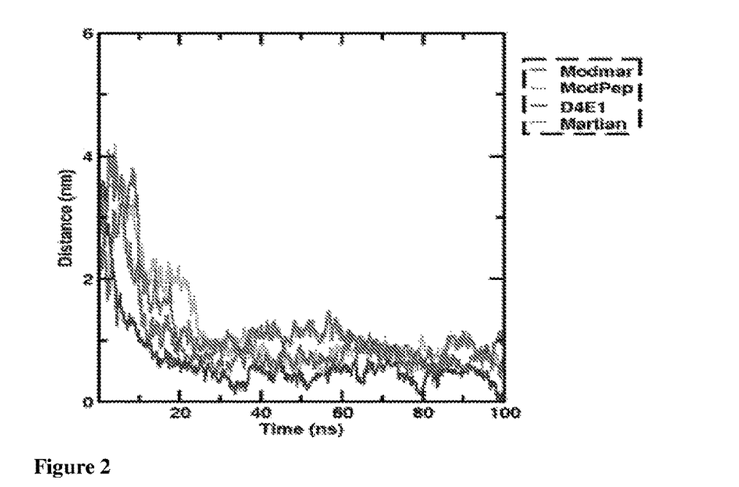
FIG. 2 depicts the distance of each peptide from the POPC bilayer; the peptides bind at 20 ns and remain stable up to 100 ns. The distances were calculated from molecular dynamics simulations using distance-measuring algorithms.
Figure 3:
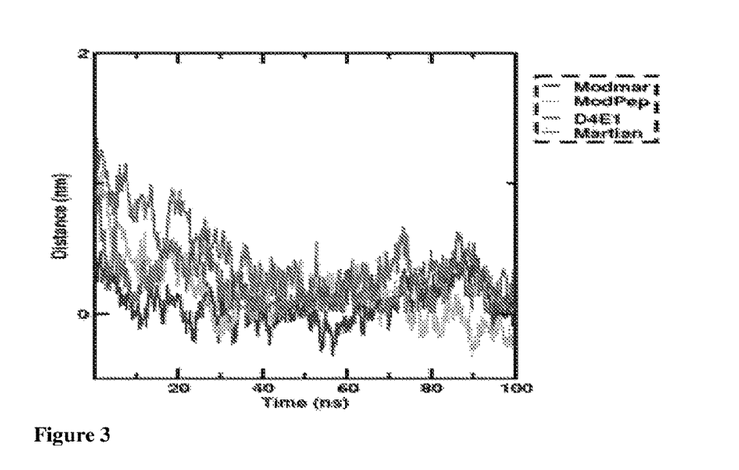
FIG. 3 depicts the distance of each peptide from the POPG bilayer; the peptides bind at 20 ns, ModPep shows high binding to the POPG bilayer. The distances were calculated from molecular dynamics simulations using distance-measuring algorithms.

Accordingly, the peptides bind to the 2-oleoyl-1-pamlitoyl-sn-glyecro-3-phosphocholine (POPC) bilayer and 2-oleoyl-1-pamlitoyl-sn-glyecro-3-phosphoglycerol (POPG) bilayer. SEQ. ID. NO: 1 is shown to have a higher binding ability to the POPG bilayer. The distance of the peptides from the bilayer is analysed by using distance-measuring algorithms in FIG. 3.

Inhibition of cell membrane mechanism of bacteria disintegrates the functioning of the entire cell and inhibits infections in a subject. Multiple resistant micro-organisms are susceptible to the present anti-microbial peptides, in view of its cell binding affinity to the cell membrane.

In yet another preferred embodiment, the present invention provides that the said peptides having sequences of SEQ. ID. NO: 1, SEQ. ID. NO: 2 and SEQ. ID. NO: 3 inhibit the activity of pathogenic micro-organisms selected from the group consisting of bacterial pathogens such as *Staphylococcus aureus, Pseudomonas aeruginosa, Escherichia coli* and *Salmonella enterica* and fungal human pathogens, *Candida albicans, Cryptococcus neoformans, Aspergillus niger* and fungal plant pathogens, *Fusarium oxysoprum, Neurospora crassa* and *Ustilago maydis*.

In Vitro Studies

In another embodiment, the instant anti-microbial peptides have anti-fungal mechanisms such as reactive oxygen species (ROS) generation, membrane damage and yeast hypha transition inhibition activity.

Accordingly, human and plant pathogens are sensitive to the present peptides having a variable Minimum Inhibitory Concentration (MIC) in the range of 1-256 µg/ml.

The Gram positive as well as the Gram negative bacterial cultures were found to be sensitive to all the peptides tested. The MIC values are at par to the ampicillin (positive control) as observed in Table 8.

Apart from the synthetic method to obtain the present synthetic peptides, nucleic acid molecules encoding the said peptides are obtained by screening natural sources for the presence of the same, or may be obtained by automated synthesis of nucleic acid molecules, by using the polymerase chain reaction (PCR) with oligonucleotide primers having nucleotide sequences that are based upon known nucleotide sequences of the antimicrobial peptide genes.

Using recombinant DNA techniques the nucleotide sequence encoding the either of the said peptides is inserted into an expression vector. The vector carrying the DNA sequence encoding the said peptides should contain a promoter sequence, and other regulatory sequences including an enhancer, ribosome binding site, transcription termination signal sequence, secretion signal sequence, origin of replication, selectable marker, and the like. The regulatory sequences are linked with one another to facilitate transcription and subsequent translation to obtain the said peptides.

In one more embodiment, the present invention provides the use of the present anti-microbial composition in the prevention and treatment of bacterial infections in a subject.

Accordingly, the present composition may be used against both Gram positive and Gram-negative bacteria causing human infections.

Another use of the present anti-microbial composition is its applications in the prevention of damages made to agricultural produce by fungal pathogens. In other embodiments, the present invention provides a method of treating a subject diagnosed with bacterial infections by administrating a therapeutically effective amount of the present composition to the subject in need thereof.

The present invention also provides a method of treating a subject diagnosed with fungal infections by administrating a therapeutically effective amount of the present composition to a subject in need thereof.

Alternatively, the invention also provides a method of preventing damage to agricultural produce by fungal pathogens by contacting the agricultural produce with an effective amount of the present composition.

The method comprises bringing the agricultural produce in contact with the present composition by spraying foliage and agricultural products with an effective amount of the said composition.

EXAMPLES

The following examples, which include preferred embodiments, will serve to illustrate the practice of this invention, it being understood that the particulars shown are by way of example and for purpose of illustrative discussion of preferred embodiments of the invention.

Example 1

Synthesis of Anti-Microbial Peptides:

TABLE 1

| No. | Peptide | Sequence | No of Amino Acids |
|---|---|---|---|
| 1 | ModPep | FRLKLHLKLRLKLHLKK (SEQ. ID. NO: 1) | 17 |
| 2 | Martian | FRLKFHLKF (SEQ. ID. NO: 2) | 9 |
| 3 | Modified Martian | VLKKLKKLC (SEQ. ID. NO: 3) | 9 |

Example 2

Experimental Methodology:
Physicochemical Properties:

Optimization of the designed peptides was done based on physicochemical properties pertaining to the antimicrobial peptide.

i. The molecular weight, net charge, isoelectric point for the peptides were calculated using the PhytAMP database (phytamp.pfba-lab-tun.org/tools.php).

TABLE 2

| Net charge on the peptides | |
|---|---|
| Peptide | Net charge |
| SEQ. ID. NO: 2 | 4 |
| SEQ. ID. NO: 3 | 4 |
| SEQ. ID. NO: 1 | 9 | ii. The Aliphatic Index, Instability index and the probability of forming an antimicrobial peptide were calculated using the CAMP database (www.bicnirrh.res.in/antimicrobial/program.php).

Aliphatic Index—Relative protein volume occupied by aliphatic side chains.

Instability Index—The instability index is a measure of proteins used to determine whether it will be stable in test tube.

TABLE 3

| Peptide | Aliphatic index [high is good] | Instability index [low is good] |
|---|---|---|
| SEQ ID NO: 2 | 86.67 | −9.98 |
| SEQ ID NO: 3 | 162.22 | −28.84 |
| SEQ ID NO: 1 ModPep | 160.59 | −14.22 |

The Probability of forming an Antimicrobial peptide is checked by support Vector Machine. In machine learning support vector machines are supervised learning models with associated learning algorithms that analyze data and recognize patterns, used for classification and regression analysis.

TABLE 4

| Peptide | Probability of forming AMP 0-1 Range good |
|---|---|
| SEQ ID NO: 2 | .999 |
| SEQ ID NO: 3 | .960 |
| SEQ ID NO: 1 | .999 | iii. The Mean hydrophobicity and Mean hydrophobic moment were calculated using HydroMcalc (www.bbcm.univ.trieste.it/~tossi/HydroCalc/HydroMCalc.html).

TABLE 5

| Peptide | Hydrophobic moment | Helix Propensity (%) | Boman Index-Protein Binding Index (kcal/mol) |
|---|---|---|---|
| SEQ. ID. NO: 2 | 0.66 | 0.05 | 0.23 |
| SEQ. ID. NO: 3 | 4.78 | 0.12 | 1.32 |
| SEQ. ID. NO: 1 | 1.07 | 5.58 | 1.73 | iv. The percentage of hydrophobic residues and the boman index was calculated using the APD database (aps.unm-c.edu/AP/prediction/prediction_main.php).

v. The Helical forming propensity was calculated using the AGADIR program (agadir.crg.es/protected/academic/calculation.jsp)

Example 3

Structural Analysis of Peptides:

The mass peptide analysis of the instant anti-microbial peptides were synthesized by ESI-MS spectral analysis.

TABLE 6

Quality control specifications for peptide mass analysis:

| Test | Specifications |
|---|---|
| Physical appearance | White lyophilized powder |
| Solubility | Soluble in milli Q water |
| Purity (HPLC) | >90% (93% as per HPLC chromatogram) |
| Injection volume | Approximately 1 mg/ml peptide in milli Q water, 20 μl per injection |
| HPLC conditions | HPLC buffers:<br>A. milli Q water with 0.1% TFA.<br>B. 80% acetonitrile with 0.1% TFA. |
| Mass | Performed ESI-MS mass spectral analysis Mass obtained as 1072.1 Da and its $2^{nd}$ to $4^{th}$ fragments are 536.7 Da, 358.3 Da and 269 Da respectively. |

TABLE 7

Structural analysis of SEQ. ID. NO: 1

| Sequence | Phe-Arg-Leu-Lys-Leu-His-Lys-Leu-Lys-Arg-Leu-Lys-Leu-His-Leu-Lys-Lys-NH$_2$ |
|---|---|
| Molecular formula | C$_{105}$H$_{188}$N$_{34}$O$_{17}$ |
| Molecular weight | 2199 Da |
| Quantity | 19 mg |

TABLE 8

Structural analysis of SEQ. ID. NO: 2

| Sequence | Phe-Arg-Leu-Lys-Phe-His-Leu-Lys-Phe-NH$_2$ |
|---|---|
| Molecular formula | C$_{63}$H$_{95}$N$_{17}$O$_9$ |
| Molecular weight | 1234.6 Da |
| Quantity | 16 mg |

TABLE 9

Structural analysis of SEQ. ID. NO: 3

| Sequence | Val-Leu-Lys-Lys-Leu-Lys-Lys-Leu-Cys-NH$_2$ |
|---|---|
| Molecular Formula | C$_{50}$H$_{98}$N$_{15}$O$_9$S |
| Molecular weight | 1071.5 Da |
| Quantity | 16 mg |

Example 4

In-Vitro Studies i. Membrane Damage and ROS Generation

Figure 6:
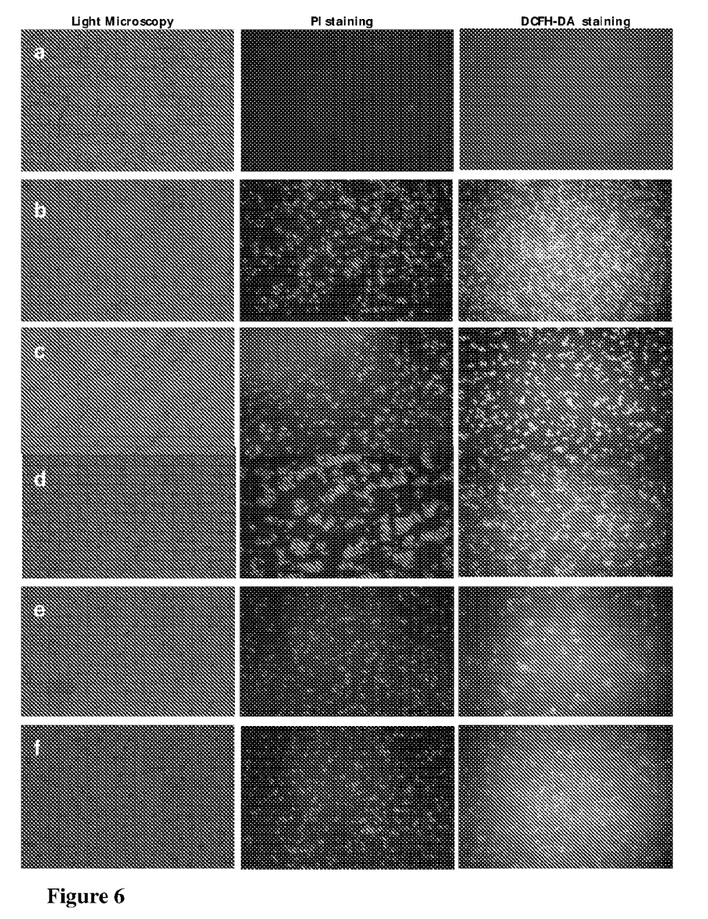
FIG. 6 depicts the membrane damage and reactive oxygen species (ROS) generation by the instant peptides (a) Untreated Control, (b) positive control (c) D4E1 (known peptide sequence, not novel, not to be covered in the invention, was used only for comparison), (d) SEQ. ID. NO: 2, (e) SEQ. ID. NO: 3 and (f) SEQ. ID. NO: 1, after incubation of peptides at their respective MICs with the *Candida albicans* cells.

The membrane damage and formation of ROS (Reactive oxygen species) are the antifungal mechanisms of a number of antimicrobial peptides. The membrane damage (middle panel) and ROS generation by the instant peptides (right panel) were monitored after incubation of peptides at their respective MICs with the *Candida albicans* cells as depicted in FIG. 6(*a-f*). A red fluorescence resulting from the membrane impermeable DNA binding dye propidium iodide was observed indicating the membrane damage in the cells due to action of peptides under study. A green fluorescence resulting from the oxidation of dye Dichloro-dihydro-fluorescein diacetate DCFH-DA (non-fluorescent molecule) into DCF 2',7'-dichlorofluorescein (fluorescent molecule) was observed indicating the presence of ROS.

The peptides D4E1 (a synthetic peptide disclosed in the art) (c) and SEQ. ID. NO: 2 (d) were found to be more potent than SEQ. ID. NO: 3 (e) and SEQ. ID. NO: 1 (f). Though all the peptides damage the membrane, the ROS generation was found to be higher in D4E1 (not novel) and SEQ. ID. NO: 2 only.

TABLE 10

| Untreated Control | 0 |
|---|---|
| Positive Control | >99% |
| D4E1 (not novel) | 95.2% |
| Martian SEQ. ID. NO: 2 | 5.88% |
| ModMar SEQ. ID. NO: 3 | 87.5% |
| ModPep SEQ. ID. NO: 1 | 92.2% | ii. Yeast-Hypha Transition Inhibition.

The peptides were also tested for the Yeast-Hypha transition inhibition. In many human and plant pathogenic fungi direct correlation between the ability of fungus to switch between yeast (Y) and hypha (H) forms and pathogenicity have been reported (Jacobsen et al, 2012; Thompson et al., 2011; Nadal et al, 2008). Except SEQ. ID. NO: 2, all the peptides inhibited Y-H transition (>85%) at 4 μg/ml (much lower than the MIC 90).

iii. In Vitro Antifungal Assays

In vitro antifungal assays were performed in RPMI-1640 medium by broth micro dilution according to the Clinical and Laboratory Standards Institute (CLSI, formerly NCCL) methods M27-A3 and M-38-A2. All the tested cultures were sensitive to the peptides with variable MIC values (2-256 μg/ml) as observed in Table 7. The peptides D4E1 (not novel) and SEQ. ID. NO: 2 were found to be most potent against all the cultures tested. The peptide SEQ. ID. NO: 3 showed moderate activity whereas peptide SEQ. ID. NO: 1 was found to be least effective. Peptides D4E1 (not novel) and SEQ. ID. NO: 2 are better candidates for the control of human as well as plant pathogenic fungi. Amphotericin B was used as positive control.

TABLE 11

Inhibitory activity of antimicrobial peptides against human and plant pathogens.

| | MIC 90 (μg/ml) | | | |
|---|---|---|---|---|
| Strains | Ampho B | D4E1 | SEQ. ID. NO: 2 | SEQ. ID. NO: 3 | SEQ. ID. NO: 1 |
| Human pathogens | | | | | |
| *Candida albicans* | 4 | 8 | 8 | 64 | >512 |
| *Cryptococcus* | 4 | 4 | 4 | 16 | 256 |
| *Aspergillus niger* | 8 | 16 | 16 | 16 | 128 |
| Plant Pathogen | | | | | |
| *Fusarium oxysoprum* | 8 | 16 | 8 | 32 | 128 |
| *Neurospora crassa* | 4 | 8 | 8 | 16 | 128 |
| *Ustilago maydis* | 4 | 32 | 16 | 32 | 256 |

The Gram positive as well as the Gram negative bacterial cultures was found to be sensitive to all the peptides tested. The MIC values are at par to the ampicillin (positive control) as observed in Table 8. The peptides D4E1 and Martian (SEQ. ID. NO: 2) showed similar potency towards Gram positive and Gram negative whereas Mod Mar (SEQ. ID. NO: 3) showed higher potency towards Gram positive as compared to Gram negative bacteria; Mod PEP (SEQ. ID. NO: 1) was found to be more potent for Gram negative than Gram positive bacteria.

TABLE 12

Inhibitory activity of Antimicrobial peptides against Gram positive and Gram negative bacteria.

| Strains | MIC 90 (µg/ml) | | | | |
|---|---|---|---|---|---|
| | Ampicillin | D4E1 | SEQ. ID. NO: 2 | SEQ. ID. NO: 3 | SEQ. ID. NO: 1 |
| Gram Positive | | | | | |
| Staphylococcus aureus | 2 | 2 | 2 | 4 | 16 |
| Pseudomonas aeruginosa | 2 | 2 | 2 | 4 | 16 |
| Gram Negative | | | | | |
| Escherichia coli | 4 | 2 | 2 | 2 | 4 |
| Salmonella enterica | 4 | 2 | 2 | 2 | 4 |

Example 5

Cytotoxicity Assays:

The toxicity of the present cationic, alpha-helical antimicrobial peptides on blood cells to determine their suitability for systemic application was performed. Lysis of erythrocyte membranes was determined by monitoring the release of haemoglobin from human erythrocyte suspensions in PBS, in relation to complete (100%) haemolysis. Table 13(a) provides the % hemolytic activity observed when a series of concentrations of the present peptides were brought in contact with erythrocytes. There was absence of any hemolytic activity up to concentrations in the range of 130 to 200 µg/mL. However at concentration above 250 µg/mL, a minimal level of hemolysis was observed.

TABLE 13 (a)

Hemolytic activity

| Concentration (µg/mL) | SEQ. ID. NO: 2 | SEQ. ID. NO: 3 | SEQ. ID. NO: 1 |
|---|---|---|---|
| 4 | — | — | — |
| 8 | — | — | — |
| 16 | — | — | — |
| 32 | — | — | — |
| 64 | — | — | — |
| 128 | — | — | — |
| 256 | 2% | 2% | 2.2% |
| 512 | 3.2% | 2.9% | 4.0% |
| 1024 | 7% | 5.7% | 5.8% |

The cytolytic activity of the present peptides was assessed by the MTT (3-(4,5-dimethylthiazol-2-yl)-2,5-diphenyltetrazolium bromide) assay against human cell lines (Hela cells). The cytotoxicity of on HeLa cells was assessed. Approximately $10^4$ cells per well were seeded in a 96-well plate and incubated for 12-16 h at 37° C.

The % viability observed below is in the range of 75% to 100% thereby confirming its suitability to systemic administration.

TABLE 13(b)

MTT Assay

| Sample code | O.D (Control) | O.D. (Treated Cells) | % viability |
|---|---|---|---|
| SEQ. ID. NO: 1 | 0.9197 | 0.7275 | 79% |
| SEQ. ID. NO: 3 | 0.9493 | 0.8325 | 88% |
| SEQ. ID. NO: 2 | 0.956 | 1.0185 | 100% |

ADVANTAGES OF INVENTION

The present invention provides novel therapeutics in the form of the present synthetic peptides selected from SEQ. ID. NO: 1,SEQ. ID. NO: 2 and SEQ. ID. NO: 3 in combating the increasing incidence of antibiotic resistance in pathogenic microbes.

The present anti-microbial peptides are highly stable indicating that the present peptides satisfy requirements of systemic administration.

We claim:

1. An anti-microbial composition comprising one or more synthetic peptides, wherein the amino acid sequences of the synthetic peptides are selected from the group consisting of the amino acid sequence of SEQ. ID. NO: 1, SEQ. ID. NO: 2 and SEQ ID NO: 3, and wherein the composition contains with one or more pharmaceutically acceptable excipients.

2. The anti-microbial composition according to claim 1, wherein the anti-microbial peptides are cationic and comprise α-helix and coil structures.

3. The anti-microbial composition according to claim 1, wherein the peptides bind to the 2-oleoyl-1-pamlitoyl-sn-glyecro-3-phosphocholine (POPC) bilayer and the 2-oleoyl-1-pamlitoyl-sn-glyecro-3-phosphoglycerol (POPG) bilayer in microbial cell walls.

4. The anti-microbial composition according to claim 1, wherein the composition consists of three synthetic peptides and one or more pharmaceutically acceptable excipient, wherein the amino acid sequences of the three synthetic peptides are selected from the group consisting of SEQ. ID. NO: 1, SEQ. ID. NO: 2, and SEQ. ID. NO:3.

5. The anti-microbial composition according to claim 1, wherein the peptides have a Minimum Inhibitory Concentration (MIC) in the range of 1-256 μg/ml.

6. The anti-microbial composition according to claim 1, wherein the pharmaceutically acceptable excipients are selected from the group consisting of a solvent, a viscosity imparting agent, a buffering agent, and a humectant.

7. The anti-microbial composition according to claim 6, wherein the solvent is selected from the group consisting of water, ethanol, isopropanol and propanol.

8. The anti-microbial composition according to claim 6, wherein the viscosity imparting agent is selected from the group consisting of hydroxyethyl cellulose and hydroxypropyl methylcellulose.

9. The anti-microbial composition according to claim 6, wherein the buffering agent is selected from the group consisting of fumarates, carbonates, phosphates, and gluconates having a pH in the range of 4 to 7.

10. The anti-microbial composition according to claim 1, wherein the composition inhibits the activity of microorganisms selected from the group consisting of *Staphylococcus aureus, Pseudomonas aeruginosa, Escherichia coli, Salmonella enterica, Candida albicans, Cryptococcus neoformans, Aspergillus niger, Fusarium oxysoprum, Neurospora crassa* and *Ustilago maydis*.

11. The anti-microbial composition according to claim 1, wherein the composition is formulated as a tablet, capsule, pellet, granule, oral powder, injectable powder, syrup, solution, liquid ampoule, dispersion, aerosol spray, semi-solid, softgel, aerosol, or suspension.

12. The anti-microbial composition according to claim 11, wherein the composition is formulated as a nano or micro suspension.

13. A method of treating bacterial infections in a subject, the method comprising administrating a therapeutically effective amount of the composition of claim 1 to the subject in need thereof.

14. A method of treating a fungal infection in a subject diagnosed with the fungal infection, the method comprising administrating a therapeutically effective amount of the composition of claim 1 to the subject in need thereof.

15. A method of reducing damage to agricultural produce by fungal pathogens by contacting the agricultural produce with an effective amount of the composition of claim 1.

16. The method of reducing damage to agricultural produce by fungal pathogens according to claim 15, the method comprising spraying foliage or agricultural produce with an effective amount of the anti-microbial composition.

* * * * *

SEQUENCE LISTING

```
<160> NUMBER OF SEQ ID NOS: 3

<210> SEQ ID NO 1
<211> LENGTH: 17
<212> TYPE: PRT
<213> ORGANISM: Artificial Sequence
<220> FEATURE:
<223> OTHER INFORMATION: Synthetic antimicrobial peptide ModPep

<400> SEQUENCE: 1

Phe Arg Leu Lys Leu His Leu Lys Leu Arg Leu Lys Leu His Leu Lys
1               5                   10                  15

Lys

<210> SEQ ID NO 2
<211> LENGTH: 9
<212> TYPE: PRT
<213> ORGANISM: Artificial Sequence
```

-continued

```
<220> FEATURE:
<223> OTHER INFORMATION: Synthetic antimicrobial peptide Martian

<400> SEQUENCE: 2

Phe Arg Leu Lys Phe His Leu Lys Phe
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic antimicrobial peptide Modified
      Martian

<400> SEQUENCE: 3

Val Leu Lys Lys Leu Lys Lys Leu Cys
1               5
```